(12) United States Patent
Moon et al.

(10) Patent No.: US 9,199,890 B2
(45) Date of Patent: Dec. 1, 2015

(54) GTL-FPSO SYSTEM FOR CONVERSION OF ASSOCIATED GAS IN OIL FIELDS AND STRANDED GAS IN STRANDED GAS FIELDS, AND PROCESS FOR PRODUCTION OF SYNTHETIC FUEL USING THE SAME

(75) Inventors: Dong Ju Moon, Seoul (KR); Yun Ju Lee, Incheon (KR); Jung Shik Kang, Seoul (KR); Moonju Park, Seoul (KR); Sojung Kim, Gyeonggi-do (KR); Sang Deuk Lee, Seoul (KR); Hyunjoo Lee, Gyeonggi-Do (KR)

(73) Assignee: Korea Institute of Science and Technology, Seoul (KR)

( * ) Notice: Subject to any disclaimer, the term of this patent is extended or adjusted under 35 U.S.C. 154(b) by 701 days.

(21) Appl. No.: 12/954,072

(22) Filed: Nov. 24, 2010

(65) Prior Publication Data

US 2011/0130474 A1 Jun. 2, 2011

(30) Foreign Application Priority Data

Nov. 27, 2009 (KR) .................. 10-2009-0116000

(51) Int. Cl.
| | |
|---|---|
| *B01J 8/00* | (2006.01) |
| *C07C 1/12* | (2006.01) |
| *B01J 19/00* | (2006.01) |
| *C07C 1/04* | (2006.01) |
| *C10G 2/00* | (2006.01) |

(52) U.S. Cl.
CPC ... *C07C 1/12* (2013.01); *B01J 8/00* (2013.01); *B01J 19/0093* (2013.01); *C07C 1/0485* (2013.01); *C10G 2/32* (2013.01); *B01J 2219/00783* (2013.01); *B01J 2219/00835* (2013.01); *B01J 2219/00873* (2013.01); *C01B 2203/0227* (2013.01); *C01B 2203/061* (2013.01); *C01B 2203/062* (2013.01); *C01B 2203/066* (2013.01); *C01B 2203/86* (2013.01); *C10G 2300/1033* (2013.01); *C10G 2300/4062* (2013.01); *C10G 2300/4068* (2013.01)

(58) Field of Classification Search
None
See application file for complete search history.

(56) References Cited

U.S. PATENT DOCUMENTS

| | | | | |
|---|---|---|---|---|
| 4,116,821 | A * | 9/1978 | Peiser ........................ | 208/361 |
| 4,309,359 | A * | 1/1982 | Pinto .......................... | 518/705 |
| 5,030,339 | A * | 7/1991 | Czarnecki .................. | 208/351 |
| 5,866,751 | A * | 2/1999 | Womack et al. ........... | 585/899 |
| 5,950,732 | A * | 9/1999 | Agee et al. ................. | 166/354 |
| 6,720,359 | B2 * | 4/2004 | O'Rear et al. ............. | 518/702 |
| 7,108,070 | B2 * | 9/2006 | Hall et al. .................. | 166/357 |
| 2002/0024038 | A1 * | 2/2002 | Iijima et al. ............... | 252/373 |
| 2003/0225169 | A1 * | 12/2003 | Yetman ...................... | 518/726 |
| 2004/0122114 | A1 * | 6/2004 | Font Freide et al. ...... | 518/703 |
| 2005/0106086 | A1 * | 5/2005 | Tomlinson et al. ........ | 422/187 |
| 2008/0210596 | A1 * | 9/2008 | Litt et al. ................... | 208/20 |

FOREIGN PATENT DOCUMENTS

| | | | |
|---|---|---|---|
| WO | WO 0018680 A1 * | 4/2000 | |
| WO | WO 0061707 A1 * | 10/2000 | |

* cited by examiner

*Primary Examiner* — Jennifer A Leung
(74) *Attorney, Agent, or Firm* — Frommer Lawrence & Haug, LLP (57) ABSTRACT

Disclosed are a gas to liquids (GTL)-floating production, storage and offloading (FPSO) system that can be used in offshore oil fields or stranded gas fields and a method for producing synthetic fuel using the same. More particularly, the disclosure relates to a GTL-FPSO system capable of producing liquid synthetic fuel from gas extracted from stranded gas fields or associated gas extracted from oil fields, including a reforming reactor and a liquid hydrocarbon producer, and a method for producing the same.

10 Claims, 4 Drawing Sheets

GTL-FPSO SYSTEM FOR CONVERSION OF ASSOCIATED GAS IN OIL FIELDS AND STRANDED GAS IN STRANDED GAS FIELDS, AND PROCESS FOR PRODUCTION OF SYNTHETIC FUEL USING THE SAME

CROSS-REFERENCE TO RELATED APPLICATIONS

This application claims priority under 35 U.S.C. §119 to Korean Patent Application No. 10-2009-0116000, filed on Nov. 27, 2009, in the Korean Intellectual Property Office, the disclosure of which is incorporated herein by reference in its entirety.

BACKGROUND (a) Technical Field

The present disclosure relates to a gas to liquids (hereinafter GTL)-floating production, storage and offloading (hereinafter FPSO) system that can be used in offshore oil fields or stranded gas fields and a method for producing synthetic fuel using the same. More particularly, the disclosure relates to a GTL-FPSO system capable of producing liquid synthetic fuel from gas extracted from stranded gas fields or associated gas extracted from oil fields, including a reforming reactor and a liquid hydrocarbon producer, and a method for producing the same.

(b) Background Art

With the recent rapid increase in oil prices, there has been a growing concern on the use of alternative energy. In particular, the production of synthetic oil from natural gas buried in stranded gas fields as a new energy resource has been receiving much attention.

GTL refers to a chemical process of converting natural gas to liquid petroleum products or the products produced therefrom. Since the final product is a chemically synthesized liquid, it is distinguished from a liquefied natural gas (LNG), which is a physically liquefied natural gas by treatment of natural gas at low temperature or high pressure.

The GTL process has a few advantages. First, the product, being obtained in liquid, is easy to handle and transport, thus being applicable to offshore stranded gases or oil fields distant from the place where the product is needed. Further, the synthetic oil product produced by the GTL process passes through a desulfurization process, and thus the resulting product is a clean fuel containing free sulfur and is advantageous over petroleum or other automobile fuels when considering the environmental regulations which become stricter.

The GTL process has been applied in medium-to-large sized on-land gas fields. However, since the existing GTL process is inappropriate for medium-to-small sized stranded gas fields (0.1 to 5 Tcf: trillion cubic feet), which account for the majority of gas reserves, when considering investment costs, there is a need for an offshore compact GTL process for converting natural gas produced from medium-to-small sized stranded gas fields to a liquid fuel.

A typical GTL process is a process whereby liquid fuel or chemical products are produced via synthetic gas, i.e., a mixture of CO and $H_2$ produced by reforming of methane ($CH_4$) from natural gas. The Fischer-Tropsch (FT) synthesis of producing liquid hydrocarbons from the synthetic gas over Fe or Co catalysts is the core technology of this process.

The reforming for producing the synthetic gas is mainly achieved through reforming of methane, the major constituent of natural gas. The reforming reactions are largely classified into steam reforming, partial oxidation, autothermal reforming, carbon dioxide reforming, steam carbon dioxide reforming, or the like.

Steam reforming is a method of producing hydrogen-rich synthetic gas through a direct reaction of methane with steam in the presence of a catalyst. The chemical reaction formula of the steam reforming is as follows:

$$CH_4 + H_2O \rightarrow 3H_2 + CO \quad \Delta H = 226 kJ/mol \quad (1)$$

As indicated in the above reaction formula, steam reforming is an endothermic reaction and requires a supply of thermal energy from outside.

Unlike the steam reforming, partial oxidation is a method of producing synthetic gas by supplying oxygen. It is divided into non-catalytic partial oxidation and catalytic partial oxidation depending on the use of a catalyst. Because oxygen is needed for the process, investment cost for the oxygen plant facility is high. Further, cokes are generated as byproducts because the reaction is performed at high temperature. The chemical reaction formula of the partial oxidation is as follows:

$$CH_4 + \tfrac{1}{2}O_2 \rightarrow 2H_2 + CO \quad \Delta H = -44 kJ/mol \quad (2)$$

In autothermal reforming, steam reforming and partial oxidation occur at the same time. The chemical reaction formula is as follows:

$$CH_4 + \tfrac{1}{2}O_2 + H_2O \rightarrow 3H_2 + CO_2 \quad \Delta H = -18 kJ/mol \quad (3)$$

Carbon dioxide reforming is a method of producing synthetic gas by reacting methane with carbon dioxide. The reaction formula is as follows:

$$CH_4 + CO_2 \rightarrow 2H_2 + 2CO \quad \Delta H = 261 kJ/mol \quad (4)$$

Steam carbon dioxide reforming is a method of producing synthetic gas by reacting methane with steam and carbon dioxide. The reactions of the reaction formulae (1) and (4) occur at the same time.

Tri-reforming is a process of producing synthetic gas by reacting methane with steam, carbon dioxide and oxygen. The reactions of the reaction formulae (1), (2) and (4) occur at the same time.

Since the facility for producing the synthetic gas accounts for a large portion of investment cost in the whole GTL plant, selection of an appropriate production method is made in consideration of source materials, scales of the facility and other technical aspects in order to reduce the cost.

The Fischer-Tropsch synthesis is a process of converting the synthetic gas consisting of $H_2$ and CO into linear paraffinic hydrocarbons via chain growth reactions in the presence of Fe- or Co-based catalysts [reaction formula (5)].

Although linear paraffinic hydrocarbons are produced as main products of the Fischer-Tropsch synthesis, α-olefins ($C_nH_{2n}$) having double bonds or alcohols are also produced as byproducts. Further, unwanted side reactions including conversion of the synthetic gas to methane [methanation; reaction formula (6)], water-gas shift reaction [reaction formula (7)] and coking which results in deactivation of the catalyst [Boudouard reaction, reaction formula (8)] may occur. The products of the Fischer-Tropsch synthesis include primary products and secondary products which result, for example, from readsorption and isomeric carbon chain growth of the primary products (mainly α-olefins).

FT synthesis (chain growth)

$$CO + 2H_2 \rightarrow -CH_2- + H_2O \quad \Delta H(227°C) = -165 kJ/mol \quad (5)$$

Methanation $$CO + 3H_2 \rightarrow CH_4 + H_2O \quad \Delta H(227°C) = -215 kJ/mol \quad (6)$$

Water-Gas Shift $$CO+H_2O \leftrightarrow CO_2+H_2 \; \Delta H(227°\,C.)=-40\,kJ/mol \quad (7)$$

Boudouard Reaction $$2CO \leftrightarrow C+CO_2 \; \Delta H(227°\,C.)=-134\,kJ/mol \quad (8)$$

In general, the high-boiling wax products produced during the Fischer-Tropsch synthesis may be further reformed (upgraded) for example by hydrocracking to give fuel with a low boiling point.

Floating, production, storage and offloading (FPSO) refers to a floating system for producing and storing oil and gas and then offloading to a transportation system.

FPSO includes an apparatus for drilling crude oil and an oil/gas separating apparatus for separating glassy oil into crude oil and associated gas. Further, FPSO includes a storage apparatus for storing the crude oil and an offloading apparatus for transporting the crude oil.

Recently, a self-powered FPSO system is used because of the necessity for moving to perform production of crude oil.

The associated gas produced during the FPSO process is either flared and then released to the atmosphere or compressed and then reinjected into the oil wells. Thus, GTL-FPSO or LNG-FPSO may be considered to utilize the associated gas from the oil fields as a raw material of the GTL process or the LNG process at FPSO. The natural gas directly extracted from the stranded gas fields may be converted into a synthetic fuel via a GTL-FPSO process or may be directly liquefied via an LNG-FPSO process.

Accordingly, it is important to develop a cost-effective process to utilize the stranded gas from medium-to-small sized stranded gas fields of about 0.1 to 5 Tcf, which account for the majority of gas reserves, and the associated gas from offshore oil fields. In particular, there is an urgent need for the development of a compact GTL-FPSO process, which is so economical as to recover the investment cost for converting natural gas to a synthetic fuel.

In addition, there is a need for the development of a system enabling water-gas shift to adjust the proportion of CO and $H_2$ required for the Fischer-Tropsch synthesis or separating $H_2$ in part from the synthetic gas and cracking high-boiling waxes for use as a source material.

SUMMARY

The inventors of the present invention have developed a gas to liquids (GTL)-floating, production, storage and offloading (FPSO) system for converting associated gas from offshore oil fields or natural gas from stranded gas fields and a method for producing a synthetic fuel using the same. The GTL-FPSO system includes a reforming reactor for producing synthetic fuel from associated gas from oil fields and natural gas from stranded gas fields on an FPSO vessel, a liquid hydrocarbon producer, an upgrading reactor and an internal power generator. A hydrogen separator and a carbon dioxide separation unit are provided between the reforming reactor and the liquid hydrocarbon producer, and a water separator is provided between the liquid hydrocarbon producer and the upgrading reactor, such that the separated water and carbon dioxide and the water and carbon dioxide produced from the power generation system are recycled into the reforming reactor.

In one aspect, the present disclosure provides a GTL-FPSO system for offshore oil fields, including: an FPSO facility including a glassy oil separator and an oil/gas separation unit; a reforming reactor; a liquid hydrocarbon producer; an upgrading reactor; a subsea storage of carbon dioxide; and an internal power generator, wherein a hydrogen separator and a carbon dioxide separation unit are provided between the reforming reactor and the liquid hydrocarbon producer and a water separator is provided between the liquid hydrocarbon producer and the upgrading reactor, such that separated water and carbon dioxide, and water and carbon dioxide produced by the internal power generator are recycled to the reforming reactor and surplus carbon dioxide is stored in the used oil and/or gas fields.

In another aspect, the present disclosure provides a GTL-FPSO system for offshore stranded gas fields, including: an FPSO facility; a reforming reactor; a liquid hydrocarbon producer; an upgrading reactor; a subsea carbon dioxide storage; and an internal power generator, wherein a hydrogen separator and a carbon dioxide separation unit are provided between the reforming reactor and the liquid hydrocarbon producer and a water separator is provided between the liquid hydrocarbon producer and the upgrading reactor, such that separated water and carbon dioxide, and water and carbon dioxide produced by the internal power generator are recycled to the reforming reactor and surplus carbon dioxide is stored in the used oil and/or gas fields.

The internal power generator may be a polymer electrolyte membrane fuel cell, a solid oxide fuel cell or a molten carbonate fuel cell.

The reforming reactor may be one or more reactor(s) selected from a steam reforming reactor, a partial oxidation reactor, an autothermal reforming reactor, a carbon dioxide reforming reactor, a steam carbon dioxide reforming reactor and a tri-reforming reactor, which is(are) being made compact as a fixed bed. Specifically, a compact steam reforming reactor or a steam carbon dioxide reforming reactor may be used.

The liquid hydrocarbon producer may be one or more compact reactor(s) selected from a Fischer-Tropsch reactor, a dimethyl ether reactor and a methanol reactor.

In another aspect, the present disclosure provides a method for producing synthetic fuel using a GTL-FPSO system for offshore oil fields, including: separating crude oil and gas at an FPSO facility and storing the separated crude oil in a crude oil storage; pretreating the separated gas by saturation and desulfurization; reforming the saturated and desulfurized gas with carbon dioxide and steam to produce synthetic gas including carbon monoxide and hydrogen; providing the separation of hydrogen from the purified synthetic gas; providing the separated hydrogen to an upgrading reactor, and removing carbon dioxide from the remaining synthetic gas and returning the removed carbon dioxide to be used as a reaction source of the reforming; chemically reacting the hydrogen with the carbon monoxide to produce liquid hydrocarbon, while separating water produced during the process and using the same as cooling water to remove reaction heat thereby producing steam, the steam being recycled to be used for the reforming; upgrading the liquid hydrocarbon and wax with the hydrogen provided to the upgrading reactor; producing electric power by operating a fuel cell using the synthetic gas or hydrogen, with water and carbon dioxide being produced during the process; and producing steam using the water produced by the fuel cell as cooling water and recycling the same to a reforming reactor along with the produced carbon dioxide.

In another aspect, the present disclosure provides a method for producing synthetic fuel using a GTL-FPSO system for offshore stranded gas fields, including: pretreating gas by saturation and desulfurization; reforming the saturated and desulfurized gas with carbon dioxide and steam to produce synthetic gas including carbon monoxide and hydrogen; providing the separation of hydrogen from the modified synthetic gas; providing the separated hydrogen to an upgrading reactor, and removing carbon dioxide from the remaining synthetic gas and returning the removed carbon dioxide to be used as a reaction source of the reforming; chemically reacting the hydrogen with the carbon monoxide to produce liquid hydrocarbon, while separating water produced during the process and using the same as cooling water to remove reaction heat thereby producing steam, the steam being recycled to be used for the reforming; upgrading the liquid hydrocarbon and wax with the hydrogen provided to the upgrading reactor; producing electric power by operating a fuel cell using natural gas, the synthetic gas or hydrogen, with water and carbon dioxide being produced during the process; and producing steam using the water produced by the fuel cell as cooling water and recycling the same to a reforming reactor along with the produced carbon dioxide.

The liquid hydrocarbon may be hydrocarbon produced by the Fischer-Tropsch reaction, dimethyl ether produced by a reaction of the following reaction formula (15) or methanol produced by a reaction of the following reaction formula (16):

$$2CO+4H_2 \rightarrow 2CH_3OH \rightarrow CH_3OCH_3+H_2O \quad (15)$$

$$CO+2H_2 \rightarrow CH_3OH \quad (16)$$

When the liquid hydrocarbon is produced by the Fischer-Tropsch reaction, a process of adjusting the composition of the synthetic gas required depending on the reforming or the particular catalyst system by the water-gas shift reaction or the reverse water-gas shift reaction may be included. Through this, the production yield of the liquid hydrocarbon may be improved.

The upgraded hydrocarbon may be separated and hydrocarbons with 1 to 4 carbon atoms may be returned to the reforming reactor as a combustion gas for supplying heat to the reactor for production of the synthetic gas and hydrocarbons with 5 or more carbon atoms may be stabilized and stored in a fuel storage of the FPSO facility.

In consideration of the increased demand and cost competitivity of liquified petroleum gas (LPG), LPG components with 3 or 4 carbon atoms are separated form the hydrocarbons with 1 to 4 carbon atoms and only hydrocarbons with 1 or 2 carbon atoms are returned to the reforming reactor. And, hydrocarbons with 5 or more carbon atoms may be stabilized and stored in the fuel storage of the FPSO facility.

The above and other aspects and features of the present disclosure will be infra.

BRIEF DESCRIPTION OF THE DRAWINGS

The above and other objects, features and advantages of the present disclosure will now be described in detail with reference to certain exemplary embodiments thereof illustrated in the accompanying drawings which are given hereinbelow by way of illustration only, and thus are not limitative of the disclosure, and wherein.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

In the figures, reference numerals refer to the same or equivalent parts of the disclosure throughout the several figures of the drawings.

DETAILED DESCRIPTION

Hereinafter, reference will now be made in detail to various embodiments of the present disclosure, examples of which are illustrated in the accompanying drawings and described below. While the disclosure will be described in conjunction with exemplary embodiments, it will be understood that the present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The present disclosure relates to a gas to liquids (GTL)-floating production, storage and offloading (FPSO) system producing synthetic fuel from gas or glassy oil extracted from stranded gas fields or offshore oil fields using a reforming reactor, a liquid hydrocarbon producer, or the like, and a method for producing the same.

The GTL-FPSO system mainly comprises a pretreatment apparatus pretreating natural gas, a compact reforming reactor producing synthetic gas, a liquid hydrocarbon producer producing liquid hydrocarbon from the synthetic gas, an upgrading reactor upgrading the produced liquid hydrocarbon, a hydrogen separator for upgrading, a carbon dioxide separation unit for the Fischer-Tropsch, a subsea carbon dioxide storage, and a fuel cell for producing electric power required by a water-gas shift reactor or a reverse water-gas shift reactor.

In particular, since the reforming reactor and the liquid hydrocarbon producer occupying large volume in the GTL-FPSO system of the present disclosure involve exothermic and endothermic reactions, respectively, an optimized system considering the reactors is required.

In the present disclosure, to perform continuous heat exchange through repeated chemical reactions, a compact fixed bed type heat exchanger is equipped at the reforming reactor or the liquid hydrocarbon producer to make the system compact.

In the GTL-FPSO system of the present disclosure, separation of hydrogen from the synthetic gas may be achieved by membrane separation, pressure swing adsorption, cryogenic separation or absorption. Specifically, membrane separation or pressure swing adsorption may be employed.

And, separation of carbon dioxide from the synthetic gas may be achieved by pressure swing adsorption, absorption, cryogenic separation, membrane separation, hybrid separation, or the like. Specifically, membrane separation or hybrid separation may be employed.

Figure 1:
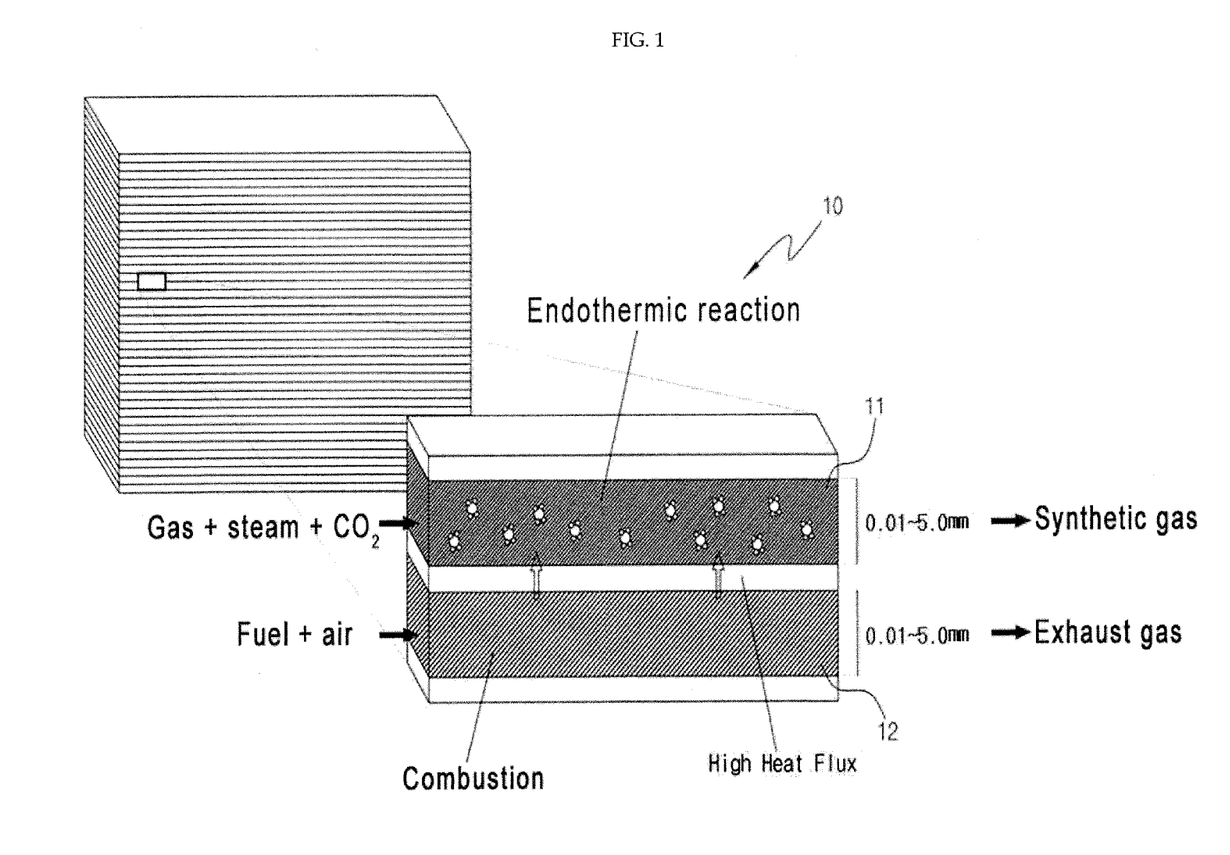
FIG. 1 shows a perspective view and a partial cross-sectional view of a compact steam carbon dioxide reforming reactor according to an embodiment of the present disclosure.

FIG. 1 shows a microchannel type steam carbon dioxide reforming reactor as an example of a compact fixed bed type reforming reactor for improving reforming efficiency according to an embodiment of the present disclosure.

The microchannel type reactor is a small reactor including a microchannel heat exchanger configured to improve thermal conductivity and maximize reactor performance. The microchannel type reactor has a plurality of metal plates formed as channels. That is to say, channels formed by etching a plurality of metal plates are arranged perpendicularly or parallelly to each other, so that fluid may flow therethrough while allowing catalytic reactions and heat exchange at the same time.

The reactions occurring at the microchannel type steam carbon dioxide reforming reactor 10 are as follows:

$$CH_4+H_2O \rightarrow 3H_2+CO \quad \Delta H=226 kJ/mol \quad (1)$$

$$CH_4+CO_2 \rightarrow 2H_2+2CO \quad \Delta H=261 kJ/mol \quad (4)$$

As seen from the reaction formulae (1) and (4), since the reactions of producing the synthetic gas are endothermic reactions, a mixture 11 comprising a methane containing gas, steam and carbon dioxide is provided into a thin-walled space (layer), so that heat required for the reactions may be provided effectively. And, a mixture 12 of fuel and air is provided into another layer, so that the heat produced from the combustion of the fuel and air may be provided effectively to the former layer. As illustrated in FIG. 1, as the mixture for reforming the natural gas is provided at high speed and the heat produced from the combustion of the fuel and air is supplied thereto, synthetic gas is produced through the chemical reactions such as those of the reaction formulae (1) and (4), and the fuel and air are discharged as exhaust gas after the combustion. As shown in FIG. 1, the reforming reactor is composed of several layers, each having a width of 0.01 to 10 mm. Since a more effective heat transfer is possible as compared to the existing tube or plate type reactors, the reactor size can be reduced considerably.

Figure 2:
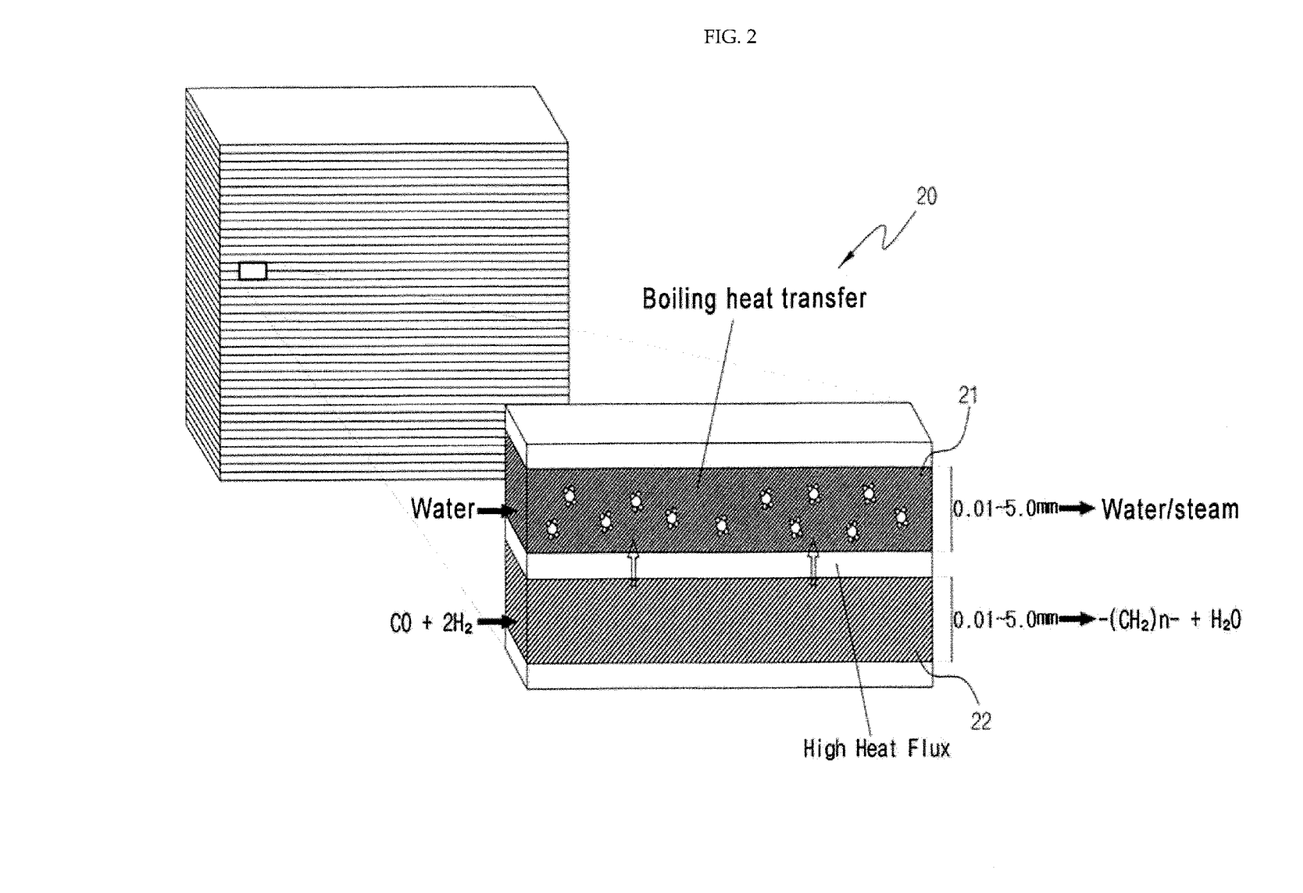
FIG. 2 shows a perspective view and a partial cross-sectional view of a compact Fischer-Tropsch reactor according to an embodiment of the present disclosure.

FIG. 2 shows a microchannel type Fischer-Tropsch reactor as an example of a compact liquid hydrocarbon producing reactor according to an embodiment of the present disclosure.

The reaction occurring in the microchannel type Fischer-Tropsch reactor is as follows:

$$CO+2H_2 \rightarrow -CH_2-+H_2O \quad \Delta H(227°\,C.)=-165 kJ/mol \quad (5)$$

As shown in FIG. 2, the microchannel type Fischer-Tropsch reactor 20 is a Fischer-Tropsch reactor having a microchannel heat exchanger with a plurality of channels 21 through which cooling water flows and a plurality of channels 22 through which synthetic gas flows stacked alternatingly. As seen from the reaction formula (5), the involved chemical reaction is an exothermic reaction. The heat produced during the reaction is absorbed by the channels through which cooling water flows. That is to say, the chemical reaction of the synthetic gas (mixture of CO and $H_2$) according to the reaction formula (5) occurs in the presence of a catalyst. As a result of the Fischer-Tropsch reaction, synthetic oil and $H_2O$ are produced, and the heat produced during the reaction is transferred to the channels through which cooling water flows and is discharged in the form of a mixture of steam and water as the cooling water is evaporated. The steam may be recycled to the reforming process. Since the microchannel type Fischer-Tropsch reactor is configured with the channels having a width of 0.01 to 10 mm, heat exchange performance is superior and the reactor size can be reduced considerably.

The GTL-FPSO system according to the present disclosure is equipped with an internal power generator. The power generation system may also be a gas turbine or a steam turbine, preferably a fuel cell device. Water and $CO_2$ produced through electrochemical reactions in the course of generating electric power by the fuel cell device may be provided to the reforming reactor to improve the yield of liquid hydrocarbon.

The fuel cell device used in the present disclosure may be a polymer electrolyte membrane fuel cell (PEMFC), a solid oxide fuel cell (SOFC) or a molten carbonate fuel cell (MCFC). The reactions occurring in a molten carbonate fuel cell are as follows:

$$\text{Anode: } H_2+CO_3^{2-} \rightarrow 2H_2O+CO_2+2e- \quad (9)$$

$$\text{Cathode: } \tfrac{1}{2}O_2+CO_2+2e^- \rightarrow CO_3^{2-} \quad (10)$$

The water produced at the anode as byproduct while the electric energy is produced from the fuel cell may be used as cooling water in the GTL-FPSO system, and the steam resulting therefrom after heat exchange may be provided to the reforming reactor along with the carbon dioxide also produced at the anode. In this case, the carbon dioxide required in the reaction at the cathode may be supplied in part from the carbon dioxide produced through the reforming and FT synthesis reactions and the carbon dioxide produced at the anode.

As another example, the fuel cell device may be a solid oxide fuel cell. The reactions occurring in the solid oxide fuel cell are as follows:

$$\text{Anode: } H_2+O^{2-} \rightarrow H_2O+2e^-, \text{ or} \quad (11)$$

$$CO+O^{2-} \rightarrow CO_2+2e^-, \text{ or} \quad (12)$$

$$CH_4+4O^{2-} \rightarrow 2H_2O+CO_2+8e^- \quad (13)$$

$$\text{Cathode: } \tfrac{1}{2}O_2+2e^- \rightarrow O^{2-} \quad (14)$$

As in the molten carbonate fuel cell, the water produced as byproduct while the electric energy is produced from the solid oxide fuel cell may be used as cooling water in the GTL-FPSO system, and the steam resulting therefrom after heat exchange may be provided to the reforming reactor. And, carbon monoxide remaining after the Fischer-Tropsch reaction or carbon dioxide produced from reforming of methane may be recycled to the reforming reactor to improve the efficiency of electric power generation by the fuel cell.

Figure 3:
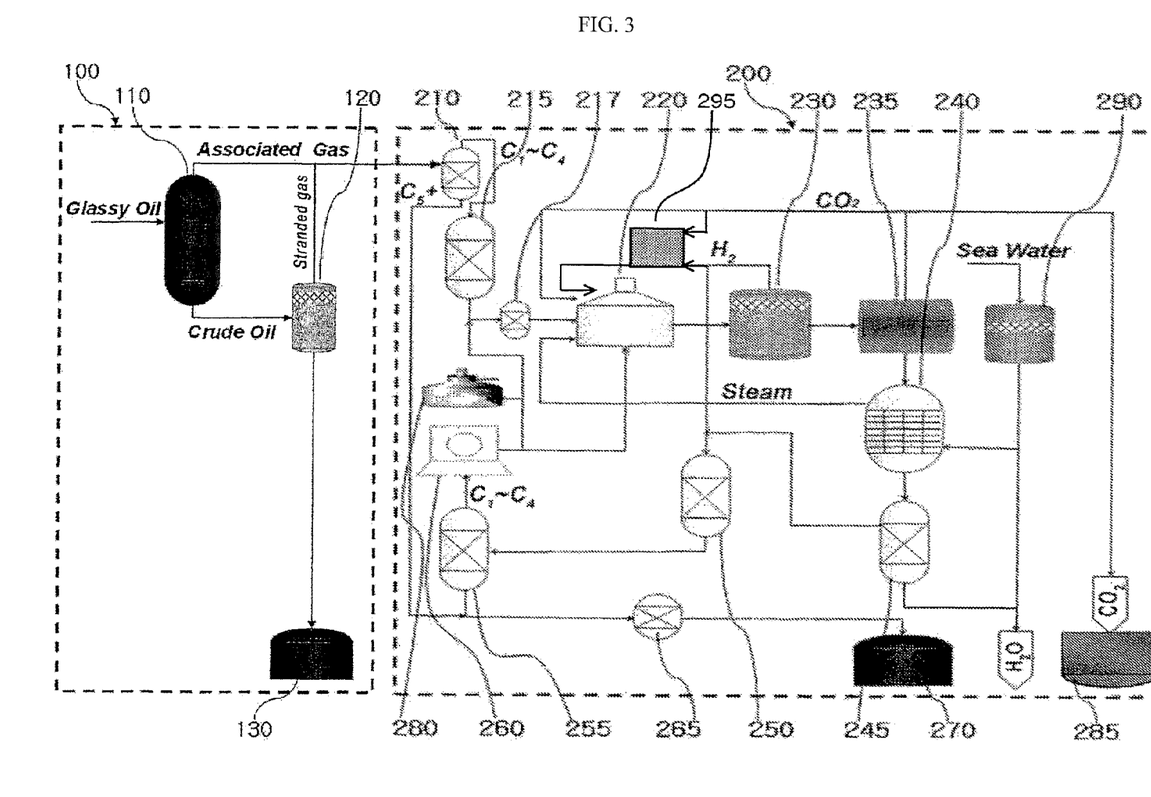
FIG. 3 shows a process of producing synthetic fuel using a GTL-FPSO system for offshore oil fields according to an embodiment of the present disclosure.

FIG. 3 shows a process of producing synthetic fuel using a GTL-FPSO system according to an embodiment of the present disclosure.

As illustrated in FIG. 3, the GTL-FPSO system comprises: an FPSO facility comprising a distiller, an oil/gas separation unit and a crude oil storage; a saturator, a hydrogenation desulfurizer, a compact reforming reactor, a compact Fischer-Tropsch reactor and an upgrading reactor for collecting the gas components separated by the FPSO facility and producing synthetic fuel; and separators for separating hydrogen, carbon dioxide, water and the product.

As seen from FIG. 3, glassy oil extracted from oil fields is separated into associated gas and crude oil by a glassy oil separator 110 of an FPSO facility 100. The separated crude oil is further separated by an oil/gas separation unit 120, such that oil is stored in a crude oil storage 130 and stranded gas is transferred via a pipe to a separator 210 of the GTL-FPSO system 200 along with the associated gas from the glassy oil separator.

After the separation by the separator 210, hydrocarbons with 5 or more carbon atoms are transferred to a stabilizer 265, and hydrocarbons with 1 to 4 carbon atoms have sulfide ($H_2S$) components removed by a desulfurizer 215 and, after passing through a prereformer 217, transferred to a compact reforming reactor 220 for reforming. Among the desulfurized hydrocarbons, those with 3 or 4 carbon atoms may be separated as liquified petroleum gas (LPG) components.

Thus produced synthetic gas may be subjected to water-gas shift reaction as described in the following reaction formula (7) to adjust the composition of CO and $H_2$ of the synthetic gas.

Water-Gas Shift $$CO + H_2O \leftrightarrow CO_2 + H_2 \ \Delta H(227° C.) = -40 kJ/mol \quad (7)$$

Further, reverse water-gas shift reaction may be performed to attain an adequate composition of CO and $H_2$.

Part of $H_2$ is separated from the produced synthetic gas by a hydrogen separator 230, and the separated $H_2$ is transferred to an upgrading reactor 250. Carbon dioxide from the remaining synthetic gas is transferred to and removed by a $CO_2$ removal unit 235. The $CO_2$ removal unit 235 separates carbon dioxide ($CO_2$). Part of the separated carbon dioxide is returned to the compact reforming reactor 220 or a fuel cell 295 to improve efficiency of electric energy production, and surplus $CO_2$ is stored in the used oil and/or gas field.

After carbon dioxide ($CO_2$) is removed, the synthetic gas comprising carbon monoxide (CO) and hydrogen ($H_2$) is transferred to a Fischer-Tropsch reactor 240 for the Fischer-Tropsch synthesis. Since the Fischer-Tropsch synthesis is an exothermic reaction, distilled water produced by treating seawater with a desalinator 290 may be used as cooling water to remove heat resulting form the Fischer-Tropsch synthesis reaction. As the cooling water absorbs the heat, part of it may be evaporated to produce steam, which may be recycled to the compact reforming reactor. The water ($H_2O$) produced by the Fischer-Tropsch synthesis may be separated by a water separator 245 and then stored or used as cooling water of the Fischer-Tropsch reactor 240. The remaining liquid hydrocarbon and wax is transferred to the upgrading reactor 250.

In the upgrading reactor 250, upgrading is carried out. For example, a hydrocarbon compound in wax form may be turned into a liquid compound having shorter chain and being easier to be transported through hydrocracking by adding hydrogen.

After being upgraded by the upgrading reactor 250, the resulting liquid hydrocarbon is transferred to a product separator 255. Compounds with 1 to 4 carbon atoms coming from an upper portion are transferred to a recycle compressor 260 and then recycled to the prereformer 217 or the compact reforming reactor 220 or are transferred to a boiler 280 to produce electric power. And, compounds with 5 or more carbon atoms coming out of a lower portion of the product separator 255 are stored transiently in the stabilizer 265 for stabilization, and the resulting synthetic fuel is then stored in a fuel storage 270.

In accordance with the present disclosure, a compact, hybrid type Fischer-Tropsch reactor is used to minimize the size of the Fischer-Tropsch reactor and the upgrading reactor. Further, $CO_2$ and $H_2O$ produced as byproducts at the fuel cell and $CO_2$ and $H_2O$ produced from the Fischer-Tropsch reaction are recycled as source materials for reforming of the natural gas. Especially, since the $H_2O$ is also used as cooling water for removing the heat produced from the Fischer-Tropsch reaction and surplus $CO_2$ is be stored in the used oil and/or gas field, the productivity of liquid hydrocarbon is improved and the cost of $CO_2$ disposal is minimized while minimizing the size of the GTL-FPSO system.

The liquid hydrocarbon producer of the present disclosure may be a dimethyl ether (DME) reactor or a methanol (MeOH) reactor rather than the Fischer-Tropsch reactor. Even in that case, the same procedure as described above may be utilized by varying process conditions such as temperature, pressure, composition of carbon monoxide (CO) and hydrogen ($H_2$), catalyst, etc.

The chemical reactions associated with the dimethyl ether reactor and the methanol reactor are as follows:

$$2CO + 4H_2 \rightarrow 2CH_3OH \rightarrow CH_3OCH_3 + H_2O \quad (15)$$

$$CO + 2H_2 \rightarrow CH_3OH \quad (16)$$

The reaction formula (15) is a chemical reaction formula for the dimethyl ether reactor, and the reaction formula (16) is a chemical reaction formula for the methanol reactor. As described in the reaction formulae (15) and (16), liquid hydrocarbon may be obtained from the synthetic gas.

Further, those skilled in the art will easily appreciate that, after crude oil is obtained from offshore oil fields, associated gas may be converted into clean liquid synthetic fuel using the GTL-FPSO system according to the present disclosure. Likewise, clean liquid synthetic fuel may be obtained from natural gas produced from stranded gas fields using the GTL-FPSO system.

The GTL-FPSO system for offshore oil fields and stranded gas fields and the method for preparing synthetic fuel as described provide the following advantageous effects.

First, associated gas from oil fields and natural gas from stranded gas fields may be converted into liquid hydrocarbon by the GTL-FPSO process without emission of $CO_2$ into the atmosphere. In addition, since surplus $CO_2$ resulting from the GTL process may be recycled to the reforming reactor or stored in the subsea storage, the cost of $CO_2$ disposal may be minimized.

Second, since surplus hydrogen or synthetic gas from the GTL-FPSO process may be utilized to produce electric power, the power required for the GTL-FPSO process for producing clean synthetic fuel may be produced offshore without environmental pollution.

Third, since water or carbon dioxide produced at the fuel cell during the production of electric energy may be recycled to the reforming reactor, the efficiency of the GTL process may be improved.

Fourth, $CO_2$ produced from the Fischer-Tropsch synthesis and the fuel cell may be recycled to the reforming reactor as a carbon source for preparation of the synthetic fuel, and water-gas (WGS) reaction or reverse WGS reaction may be performed prior to the Fischer-Tropsch synthesis in order to adjust the composition of the synthetic gas required for the Fischer-Tropsch synthesis.

Fifth, the yield of liquid hydrocarbon may be improved by separating $CO_2$ produced during the reforming and recycling it to the reforming reactor.

Sixth, since $CO_2$ produced from the Fischer-Tropsch synthesis and the fuel cell may be used as a carbon source of the synthetic fuel and surplus $CO_2$ may be stored in the subsea storage, climatic change caused by $CO_2$ emission can be prevented.

Seventh, the compact fixed bed type reactor, specifically the microchannel type reactor, provides improvement in aspects of space and cost. Further, the designing of the GTL-FPSO system may be optimized in consideration of safety issue related with the wave motion of the FPSO facility.

The present disclosure has been described in detail with reference to specific embodiments thereof. However, it will be appreciated by those skilled in the art that various changes and modifications may be made in these embodiments without departing from the principles and spirit of the disclosure, the scope of which is defined in the appended claims and their equivalents.

Figure 4:
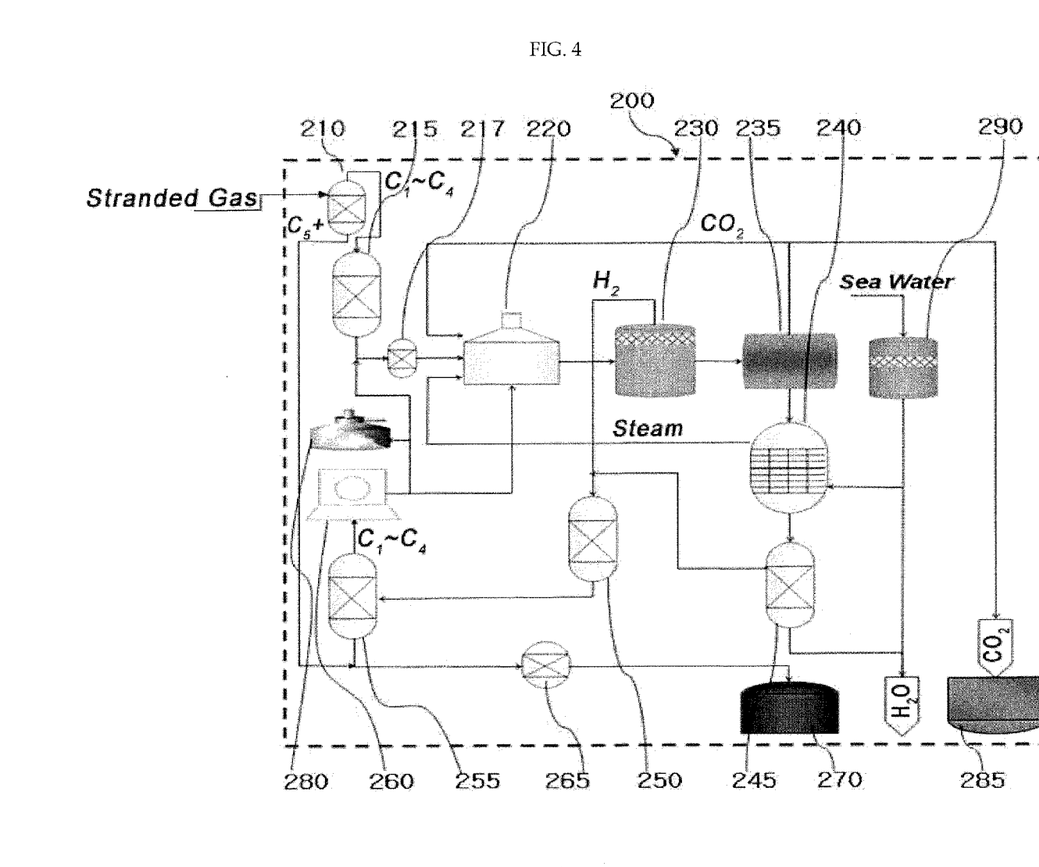
FIG. 4 shows a process of producing synthetic fuel using a GTL-FPSO system for stranded gas fields according to an embodiment of the present disclosure.

FIG. 4 is an embodiment of FPSO-GTL system 200 of the present disclosure, where FIG. 3 is an embodiment of FIG. 4, which further includes FPSO facility 100.

What is claimed is:

1. A gas to liquids (GTL)-floating, production, storage and offloading (FPSO) system for offshore oil fields, comprising:
an FPSO facility comprising a glassy oil separator and an oil/gas separation unit;
a reforming reactor;
a liquid hydrocarbon producer;
an upgrading reactor;
a subsea carbon dioxide storage; and
an internal power generator;
wherein a hydrogen separator and a carbon dioxide separation unit are provided between the reforming reactor and the liquid hydrocarbon producer and a water separator is provided between the liquid hydrocarbon producer and the upgrading reactor, such that separated water and carbon dioxide, and water and carbon dioxide produced by the internal power generator are recycled to the reforming reactor and surplus carbon dioxide is stored in the subsea carbon dioxide storage,
wherein the internal power generator includes a fuel cell that provides electrical power,
wherein liquid hydrocarbons that are upgraded by the upgrading reactor are transferred to a product separator, and compounds with 1 to 4 carbon atoms coming from the product separator are transferred to a recycle compressor that recycles the compounds to a prereformer or the reforming reactor, or the compounds are transferred to a boiler to produce electric power.

2. The GTL-FPSO system for offshore oil fields according to claim 1, wherein the internal power generator is a polymer electrolyte membrane fuel cell, a solid oxide fuel cell or a molten carbonate fuel cell.

3. The GTL-FPSO system for offshore oil fields according to claim 1, wherein the reforming reactor is one or more reactor(s) selected from a steam reforming reactor, a partial oxidation reactor, an autothermal reforming reactor, a carbon dioxide reforming reactor, a steam carbon dioxide reforming reactor and a tri-reforming reactor, the reactor(s) being made compact as a fixed bed.

4. The GTL-FPSO system for offshore oil fields according to claim 1, wherein the liquid hydrocarbon producer is one or more reactor(s) selected from a Fischer-Tropsch reactor, a dimethyl ether reactor and a methanol reactor.

5. The GTL-FPSO system for offshore oil fields according to claim 1, which further comprises:
an apparatus for circulating water from the liquid hydrocarbon producer to remove heat produced from the liquid hydrocarbon producer; or
an apparatus for desalinating seawater to be used as cooling water to remove heat produced from the liquid hydrocarbon producer.

6. A gas to liquids (GTL)-floating, production, storage and offloading (FPSO) system for offshore stranded gas fields, comprising:
an FPSO facility;
a reforming reactor;
a liquid hydrocarbon producer;
an upgrading reactor;
a subsea carbon dioxide storage; and
an internal power generator;
wherein a hydrogen separator and a carbon dioxide separation unit are provided between the reforming reactor and the liquid hydrocarbon producer and a water separator is provided between the liquid hydrocarbon producer and the upgrading reactor, such that separated water and carbon dioxide, and water and carbon dioxide produced by the internal power generator are recycled to the reforming reactor and surplus carbon dioxide is stored in the subsea carbon dioxide storage,
wherein the internal power generator includes a fuel cell that provides electrical power,
wherein liquid hydrocarbons that are upgraded by the upgrading reactor are transferred to a product separator, and compounds with 1 to 4 carbon atoms coming from the product separator are transferred to a recycle compressor that recycles the compounds to a prereformer or the compact reforming reactor, or the compounds are transferred to a boiler to produce electric power.

7. The GTL-FPSO system for offshore stranded gas fields according to claim 6, wherein the internal power generator is a polymer electrolyte membrane fuel cell, a solid oxide fuel cell or a molten carbonate fuel cell.

8. The GTL-FPSO system for offshore stranded gas fields according to claim 6, wherein the reforming reactor is one or more reactor(s) selected from a steam reforming reactor, a partial oxidation reactor, an autothermal reforming reactor, a carbon dioxide reforming reactor, a steam carbon dioxide reforming reactor and a tri-reforming reactor, the reactor(s) being made compact as a fixed bed.

9. The GTL-FPSO system for offshore stranded gas fields according to claim 6, wherein the liquid hydrocarbon producer is one or more reactor(s) selected from a Fischer-Tropsch reactor, a dimethyl ether reactor and a methanol reactor.

10. The GTL-FPSO system for offshore stranded gas fields according to claim 6, which further comprises:
an apparatus for circulating water from the liquid hydrocarbon producer to remove heat produced from the liquid hydrocarbon producer;
or an apparatus for desalinating seawater to be used as cooling water to remove heat produced from the liquid hydrocarbon producer.

* * * * *